US010245290B2

(12) United States Patent
Berggren et al.

(10) Patent No.: US 10,245,290 B2
(45) Date of Patent: Apr. 2, 2019

(54) PROBIOTIC STRAINS FOR USE IN TREATMENT OR PREVENTION OF OSTEOPOROSIS (71) Applicant: Probi AB, Lund (SE)

(72) Inventors: Anna Berggren, Flyinge (SE); Niklas Larsson, Lund (SE); Gunilla Önning, Höör (SE); Irini Lazou Ahrén, Lund (SE); Klara Sjögren, Åsa (SE); Claes Ohlsson, Västra Frölunda (SE)

(73) Assignee: Probi AB, Lund (SE)

( * ) Notice: Subject to any disclaimer, the term of this patent is extended or adjusted under 35 U.S.C. 154(b) by 107 days.

(21) Appl. No.: 14/782,138

(22) PCT Filed: Apr. 3, 2014

(86) PCT No.: PCT/SE2014/050399
§ 371 (c)(1),
(2) Date: Oct. 2, 2015

(87) PCT Pub. No.: WO2014/163568
PCT Pub. Date: Oct. 9, 2014

(65) Prior Publication Data
US 2016/0067289 A1    Mar. 10, 2016

(30) Foreign Application Priority Data

Apr. 3, 2013   (SE) ..................... 1350414
Dec. 20, 2013  (SE) ..................... 1351571

(51) Int. Cl.
*A61K 35/747* (2015.01)
*A23L 33/135* (2016.01)
*C12R 1/25* (2006.01)
*C12R 1/225* (2006.01)

(52) U.S. Cl.
CPC .......... *A61K 35/747* (2013.01); *A23L 33/135* (2016.08); *C12R 1/225* (2013.01); *C12R 1/25* (2013.01); *A23V 2002/00* (2013.01)

(58) Field of Classification Search
CPC ........ A61K 35/747; C12R 1/25; C12R 1/225; A23L 33/135; A23V 2002/00
See application file for complete search history.

(56) References Cited

U.S. PATENT DOCUMENTS

2002/0127211 A1   9/2002   Brassart et al.
2009/0208469 A1*  8/2009   Alenfall ............... A21D 2/267
                                              424/93.45

FOREIGN PATENT DOCUMENTS

| CA | 2420977 A1 | 3/2002 |
| CA | 2420977 C | 12/2010 |
| JP | 2008/544753 A | 12/2008 |
| JP | 2009-114111 A | 5/2009 |
| JP | 2009-114112 A | 5/2009 |
| JP | 2012/526551 A | 11/2012 |
| KR | 2008/0039399 A | 5/2008 |
| KR | 2013-0002543 A | 1/2013 |
| KR | 101279852 B1 | 7/2013 |
| RU | 2402341 C2 | 10/2010 |
| WO | WO 1999/002170 | 1/1999 |
| WO | WO 2001/015715 A2 | 3/2001 |
| WO | WO 2002/018542 A1 | 3/2002 |
| WO | WO 2007/004966 A1 | 1/2007 |
| WO | WO 2007/040444 A1 | 4/2007 |
| WO | WO 2010/132017 A1 | 11/2010 |

OTHER PUBLICATIONS

"Prevent"—Defined online by Oxford Dictionsaries, at the web https://en.oxforddictionaries.com/definition/prevent, accessed online on Aug. 2, 2017, p. 1.*
Vrese M., Health benefits of probiotics and prebiotics in women, Review, Menopause International, Mar. 1, 2009, vol. 15, No. 1, pp. 35-40.*
Saori M.,—JP 2009114112 A-Machine translation in English provided by STIC at USPTO, total pp. 7.*
Ali T. et al., "Osteoporosis in Inflammatory Bowel Disease", Am. J. Med., Jul. 2009, vol. 122, No. 7, pp. 599-604.*
[No Author Listed] Gastrointestinal disorders. 2015. Retrieved from http://probi.se/sites/all/files/attachment_files/gastrointestinal_disorders.pdf on Apr. 27, 2017.
[No Author Listed] Immune system. 2015.Retrieved from http://probi.se/sites/all/files/attachment_files/immune_system_2015.pdf on Apr. 27, 2017.
[No Author Listed] Increased iron absorption. Nov. 2015. Retrieved from http://probi.se/sites/all/files/attachment_files/iron_absorption_nov_2015.pdf on Apr. 27, 2017.
[No Author Listed] Metabolic syndrome. 2015. Retrieved from http://probi.se/sites/all/files/attachment_files/metabolic_syndrome.pdf on Apr. 27, 2017.
[No Author Listed] Reduced risk for osteoporosis. Nov. 2015. Retrieved from http://probi.se/sites/all/files/attachment_files/osteoporosis_nov_2015.pdf on Apr. 27, 2017.
[No Author Listed] Stress and recovery (incl. nutrient uptake). Nov. 2015. Retrieved from http://probi.se/sites/all/files/attachment_files/stress_and_recovery_nov_2015_0.pdf on Apr. 27, 2017.
Adlerberth et al., A mannose-specific adherence mechanism in Lactobacillus plantarum conferring binding to the human colonic cell line HT-29. Appl Environ Microbiol. Jul. 1996;62(7):2244-51.
Ahrné et al., The normal Lactobacillus flora of healthy human rectal and oral mucosa. J Appl Microbiol. Jul. 1998;85(1):88-94.
Antonsson et al., A comparison between the microflora of Herrgård cheese from three different dairies. International Dairy Journal. 2001;11:285-291.
Bengmark et al., Nutritional support to prevent and treat multiple organ failure. World J Surg. May 1996;20(4):474-81.

(Continued)

*Primary Examiner* — Satyendra K Singh
(74) *Attorney, Agent, or Firm* — Wolf, Greenfield & Sacks, P.C.

(57) ABSTRACT

The present invention relates to at least one probiotic strain chosen from *Lactobacillus paracasei*, or at least one probiotic strain chosen from *Lactobacillus* paracaseiin combination with at least one probiotic strain chosen from *Lactobacillus* plantarum, for use in the treatment or prevention of osteoporosis or for use in increasing the absorption of at $Ca^{2+}$ ions, in a mammal, preferably in a human.

30 Claims, 6 Drawing Sheets

(56) References Cited

OTHER PUBLICATIONS

Berggren et al., Randomised, double-blind and placebo-controlled study using new probiotic lactobacilli for strengthening the body immune defence against viral infections. Eur J Nutr. Apr. 2011;50(3):203-10. doi: 10.1007/s00394-010-0127-6.

Bering et al., A lactic acid-fermented oat gruel increases non-haem iron absorption from a phytate-rich meal in healthy women of childbearing age. Br J Nutr. Jul. 2006;96(1):80-5.

Bering et al., Viable, lyophilized lactobacilli do not increase iron absorption from a lactic acid-fermented meal in healthy young women, and no iron absorption occurs in the distal intestine. Br J Nutr. Nov. 2007;98(5):991-7.

Busch et al., Randomized, Double Blind and Placebo Controlled Study Using a Combination of Two Probiotic Lactobacilli to Alleviate Symptoms and Frequency of Common Cold. Food Nutr Sci. Nov. 2013;4(11A):13-20. doi: 10.4236/fns.2013.411A003.

Chiang et al., Effect of bioactive compounds in lactobacilli-fermented soy skim milk on femoral bone microstructure of aging mice. J Sci Food Agric. Jan. 30, 2012;92(2):328-35. doi: 10.1002/jsfa.4579.

Cunningham-Rundles et al., Development of immunocompetence: role of micronutrients and microorganisms. Nutr Rev. May 2002;60(5 Pt 2):S68-72.

Ducrotté et al., Clinical trial: Lactobacillus plantarum 299v (DSM 9843) improves symptoms of irritable bowel syndrome. World J Gastroenterol. Aug. 14, 2012;18(30):4012-8. doi: 10.3748/wjg.v18.i30.4012.

Eccles, Understanding the symptoms of the common cold and influenza. Lancet Infect Dis. Nov. 2005;5(11):718-25.

Fendrick et al., The economic burden of non-influenza-related viral respiratory tract infection in the United States. Arch Intern Med. Feb. 24, 2003;163(4):487-94.

Hoppe et al., Probiotic strain Lactobacillus plantarum 299v increases iron absorption from an iron-supplemented fruit drink: a double-isotope cross-over single-blind study in women of reproductive age. Br J Nutr. Oct. 28, 2015;114(8):1195-202. doi: 10.1017/S000711451500241X. Erratum in: Br J Nutr. Dec. 14, 2015;114(11):1948.

Johansson et al., Administration of different Lactobacillus strains in fermented oatmeal soup: in vivo colonization of human intestinal mucosa and effect on the indigenous flora. Appl Environ Microbiol. Jan. 1993:59(1):15-20.

Johansson et al., Survival of Lactobacillus plantarum DSM 9843 (299v), and effect on the short-chain fatty acid content of faeces after ingestion of a rose-hip drink with fermented oats. Int J Food Microbiol. Jun. 30, 1998;42(1-2):29-38.

Karlsson et al., Probiotic therapy to men with incipient arteriosclerosis initiates increased bacterial diversity in colon: a randomized controlled trial. Atherosclerosis. Jan. 2010;208(1):228-33. doi: 10.1016/j.atherosclerosis.2009.06.019.

King et al., Effectiveness of probiotics on the duration of illness in healthy children and adults who develop common acute respiratory infectious conditions: a systematic review and meta-analysis. Br J Nutr. Jul. 14, 2014;112(1):41-54. doi:10.1017/S0007114514000075.

Kirkpatrick, The common cold. Prim Care. Dec. 1996;23(4):657-75.

Klarin et al., Lactobacillus plantarum 299v reduces colonisation of Clostridium difficile in critically ill patients treated with antibiotics. Acta Anaesthesiol Scand. Sep. 2008;52(8):1096-102. doi: 10.1111/j.1399-6576.2008.01748.x.

Krag et al., Profermin is efficacious in patients with active ulcerative colitis-a randomized controlled trial. Inflamm Bowel Dis. Nov. 2013;19(12):2584-92. doi:10.1097/01.MIB.0000437046.26036.db.

Krag et al., Safety and efficacy of Profermin® to induce remission in ulcerative colitis. World J Gastroenterol. Apr. 21, 2012;18(15):1773-80. doi: 10.3748/wjg.v18.i15.1773.

Lavasani et al., A novel probiotic mixture exerts a therapeutic effect on experimental autoimmune encephalomyelitis mediated by IL-10 producing regulatory T cells. PLoS One. Feb. 2, 2010;5(2):e9009. doi:10.1371/journal.pone.0009009.

Lenoir-Wijnkoop et al., Public health and budget impact of probiotics on common respiratory tract infections: a modelling study. PLoS One. Apr. 10, 2015;10(4):e0122765. doi:10.1371/journal.pone.0122765.

Lomax et al., Probiotics, immune function, infection and inflammation: a review of the evidence from studies conducted in humans. Curr Pharm Des. 2009;15(13):1428-518.

Lönnermark et al., Intake of Lactobacillus plantarum reduces certain gastrointestinal symptoms during treatment with antibiotics. J Clin Gastroenterol. Feb. 2010;44(2):106-12. doi:10.1097/MCG.0b013e3181b2683f.

Mack et al., Extracellular MUC3 mucin secretion follows adherence of Lactobacillus strains to intestinal epithelial cells in vitro. Gut. Jun. 2003;52(6):827-33.

Mack et al., Probiotics inhibit enteropathogenic E. coli adherence in vitro by inducing intestinal mucin gene expression. Am J Physiol. Apr. 1999;276(4 Pt 1):G941-50.

McCracken et al., TNF-alpha sensitizes HT-29 colonic epithelial cells to intestinal lactobacilli. Exp Biol Med. Sep. 2002;227(8):665-70.

McNaught et al., A prospective randomized trial of probiotics in critically ill patients. Clin Nutr. Apr. 2005;24(2):211-9.

Molin, Lactobacillus paracasei 8700:2. Oct. 29, 2015. Dept. Food Technology, Engineering and Nutrition. Lund University. Retrieved from http://probi.se/sites/aWfiles/attachment_files/l-paracasei-8700-kolon2-15_2015-10-29_0.pdf on Apr. 27, 2017.

Molin, Lactobacillus plantarum 299. Jun. 10, 2015. Dept. Food Technology, Engineering and Nutrition. Lund University. Retrieved from http://probi.se/sites/all/files/attachment_files/lp_299-15_2015-06-10_0.pdf on Apr. 27, 2017.

Molin, Lactobacillus plantarum 299v. Oct. 29, 2015. Dept. Food Technology, Engineering and Nutrition. Lund University. Retrieved from http://probi.se/sites/all/files/attachment_files/lp_299v-15_2015-10-29_0.pdf on Apr. 27, 2017.

Molin, Lactobacillus plantarum HEAL19. Oct. 29, 2015. Dept. Food Technology, Engineering and Nutrition. Lund University. Retrieved from http://probi.se/sites/all/files/attachment_files/heal19-15_2015-10-29_0.pdf on Apr. 27, 2017.

Molin, Lactobacillus plantarum HEAL9. Oct. 29, 2015. Dept. Food Technology, Engineering and Nutrition. Lund University. Retrieved from http://probi.se/sites/all/files/attachment_files/heal9-15_2015-10-29_0.pdf on Apr. 27, 2017.

Molin, Lactobacillus rhamnosus 271. Nov. 4, 2015. Dept. Food Technology, Engineering and Nutrition. Lund University. Retrieved from http://probi.se/sites/all/files/attachment_files/l_ramnosus_271_2015_0.pdf on Apr. 27, 2017.

Niedzielin et al., A controlled, double-blind, randomized study on the efficacy of Lactobacillus plantarum 299V in patients with irritable bowel syndrome. Eur J Gastroenterol Hepatol. Oct. 2001;13(10):1143-7.

Nobaek et al., Alteration of intestinal microflora is associated with reduction in abdominal bloating and pain in patients with irritable bowel syndrome. Am J Gastroenterol. May 2000;95(5):1231-8.

Ohlsson et al., Probiotics protect mice from ovariectomy-induced cortical bone loss. PLoS One. Mar. 17, 2014;9(3):e92368. doi:10.1371/journal.pone.0092368.

Rask et al., Differential effect on cell-mediated immunity in human volunteers after intake of different lactobacilli. Clin Exp Immunol. May 2013;172(2):321-32. doi: 10.1111/cei.12055.

Sandberg, A comparative in vitro test report on calcium uptake and transport, as described in Calcium uptake and transport in Caco-2 cells in the presence of L plantarum. Sep. 13, 2012.

Sjogren et al., Probiotics Protect Mice from Ovariectomy Induced Bone-Loss. Annual Meeting of the American Society for Bone and Mineral Research (ASBMR); Baltimore, MD, USA; Oct. 4-7, 2013. Abstract available online Aug. 30, 2013.

Vasquez et al., Oral administration of Lactobacillus and Bifidobacterium strains of intestinal and vaginal origin to healthy human females: Re-isolation from faeces and vagina. Microb Ecol Health D. 2005;17(1):15-20.

[No Author Listed] Apple Mango Juice with Probiotic. MINTEL. Jul. 2012. Retrieved on Apr. 22, 2016 from http://www.gnpd.com/sinatra/recordpage/1821253/from_search/ZeoDozulyK/.

(56) References Cited

OTHER PUBLICATIONS

[No Author Listed] Orange & Lemon Flavoured Juice. MINTEL. May 2012. Retrieved on Apr. 22, 2016 from http://www.gnpd.com/sinatra/recordpage/1804868/.

[No Author Listed] Immune Booster and Stress Relief. MINTEL Apr. 2011. Retrieved on Apr. 22, 2016 from http://www.gnpd.com/sinatra/recordpage/1517037/.

Chiang et al., Antiosteoporotic effects of Lactobacillus-fermented soy skim milk on bone mineral density and the microstructure of femoral bone in ovariectomized mice. J Agric Food Chem. Jul. 27, 2011;59(14):7734-42. doi:10.1021/jf2013716. Epub Jun. 21, 2011.

Gilman et al., The effect of probiotic bacteria on transepithelial calcium transport and calcium uptake in human intestinal-like Caco-2 cells. Curr Issues Intest Microbiol. Mar. 2006;7(1):1-5.

Rayes et al., Prebiotics, probiotics, synbiotics in surgery-are they only trendy, truly effective or even dangerous? Langenbecks Arch Surg. May 2009;394(3):547-55. doi: 10.1007/s00423-008-0445-9. Epub Dec. 16, 2008.

Zebaze et al., Intracortical remodelling and porosity in the distal radius and post-mortem femurs of women: a cross-sectional study. Lancet. May 15, 2010;375(9727):1729-36. doi: 10.1016/S0140-6736(10)60320-0.

Dale et al., Rang and Dale's Pharmacology. $6^{th}$ Ed. Amsterdam: Elsevier, 2007; 469.

\* cited by examiner

A. Study Design

B. Body Weight

PROBIOTIC STRAINS FOR USE IN TREATMENT OR PREVENTION OF OSTEOPOROSIS

RELATED APPLICATIONS

This application is a national stage filing under 35 U.S.C. § 371 of International Application No. PCT/SE2014/050399, filed Apr. 3, 2014, entitled "Probiotic Strains For Use In Treatment or Prevention of Osteoporosis," which was published under PCT Article 21(2) in English and which claims priority to SE 1350414-7, filed Apr. 3, 2013 and SE 1351571-3, filed Dec. 20, 2013, the entire contents of each of which is herein incorporated by reference in its entirety.

TECHNICAL FIELD OF THE INVENTION

The present invention relates to at least one probiotic strain chosen from *Lactobacillus paracasei*, or at least one probiotic strain chosen from *Lactobacillus paracasei* in combination with at least one probiotic strain chosen from *Lactobacillus plantarum*, for use in the treatment or prevention of osteoporosis or for use in increasing the absorption of $Ca^{2+}$ ions, in a mammal, preferably in a human.

BACKGROUND ART

Osteoporosis is a disease in which bones become fragile and more likely to fracture. Usually the bone loses density, which measures the amount of calcium and minerals in the bone. Osteoporosis is the most common type of bone disease. About half of all women over the age of 50 will have a fracture of the hip, wrist, or vertebra (bone of the spine) during their lifetime. Bone is living tissue. Existing bone is constantly being replaced by new bone. Osteoporosis occurs when the body fails to form enough new bone, when too much existing bone is reabsorbed by the body, or both. Calcium is one of the important minerals needed for bones to form. If you do not get enough calcium and vitamin D, or your body does not absorb enough calcium from your diet, your bones may become brittle and more likely to fracture. A drop in estrogen in women at the time of menopause and a drop in testosterone in men is a leading cause of bone loss.

Fractures caused by osteoporosis constitute a major health concern and result in a huge economic burden on health care systems. The lifetime risk of any osteoporotic fracture is high in the western world (around 50% for women and 20% for men) and fractures are associated with significant mortality and morbidity. Cortical bone constitutes approximately 80% of the bone in the body and several studies have shown that cortical bone is the major determinant of bone strength and thereby fracture susceptibility. Bone loss after the age of 65 is mainly due to loss in cortical bone and not trabecular bone (Lancet, 2010, May 15; 375(9727): 1729-36).

The skeleton is remodeled by bone forming osteoblasts (OBs) and bone resorbing osteoclasts (OCLs). Macrophage colony stimulating factor (M-CSF) increases proliferation and survival of OCLs precursor cells as well as up-regulates expression of receptor activator of nuclear factor-KB (RANK) in OCL. This allows RANK ligand (RANKL) to bind and start the signalling cascade that leads to OCL formation. The effect of RANKL can be inhibited by Osteoprotegerin (OPG), which is a decoy receptor for RANKL.

The association between inflammation and bone loss is well established and in auto-immune diseases osteoclastic bone resorption is driven by inflammatory cytokines produced by activated T-cells. In addition, several studies demonstrate that low-grade systemic inflammation, indicated by moderately elevated serum levels of high sensitivity C-reactive protein (hsCRP), associate with low BMD, elevated bone resorption and increased fracture risk. The estrogen deficiency that occurs after menopause results in increased formation and prolonged survival of osteoclasts. This is suggested to be due to a number of factors including loss of the immunosuppressive effects of estrogen, resulting in increased production of cytokines promoting osteoclastogenesis, and direct effects of estrogen on OCLs. In line with these data, blockade of the inflammatory cytokines TNFα and IL-1 leads to a decrease in bone resorption markers in early postmenopausal women.

In recent years, the importance of the gut microbiota (GM) for both health and disease has been intensively studied. The GM consists of trillions of bacteria which collectively contain 150-fold more genes than our human genome. It is acquired at birth and, although a distinct entity, it has clearly coevolved with the human genome and can be considered a multicellular organ that communicates with and affects its host in numerous ways. The composition of the GM is modulated by a number of environmental factors such as diet and antibiotic treatments. Molecules produced by the gut bacteria can be both beneficial and harmful and are known to affect endocrine cells in the gut, the enteric nervous system, gut permeability and the immune system. Perturbed microbial composition has been postulated to be involved in a range of inflammatory conditions, within and outside the gut including Crohn's disease, ulcerative colitis, rheumatoid arthritis, multiple sclerosis, diabetes, food allergies, eczema and asthma as well as obesity and the metabolic syndrome.

Probiotic bacteria are defined as live microorganisms which when administered in adequate amounts confer a health benefit on the host and are believed to alter the composition of the gut microbiota. The suggested underlying mechanisms are manifold including increased solubility and absorption of minerals, enhanced barrier function and modulation of the immune system.

In Gilman et al, The effect of Probiotic Bacteria on Transepithelial Calcium Transport and Calcium uptake in Human Intestinal-like Caco-2 cells, Curr. Issues Intestinal Microbial. 7: 1-6, a strain of *Lactobacillus salivarius* (UCC 118) and a strain of *Bifidobacterium infantis* (UCC 35624) was tested on calcium uptake and transepithelial calcium transport in human intestinal-like Caco-2 cells in culture. Said strains had no effect on transepithelial calcium transport in fully differentiated 16-d old Caco-2 cells. Calcium uptake into the Caco-2 cell monolayers after 24 h was significantly higher in the cells exposed to *Lactobacillus salivarius*.

WO99/02170 describes the use of lactobacilli in the preparation of non-fermented enteral compositions for facilitating or increasing the absorption of minerals from the diet such as calcium, zinc, iron and magnesium. The experiments performed therein, in supporting said claimed absorption, are an in vitro model of calcium transportation using Caco-2 intestinal lines (a carcinogenic cell line).

KR101279852 discloses compositions for prevention or treatment of osteoporosis containing calcium and magnesium in addition to specific lactic acid bacterial strains such as *Streptococcus thermophilus* with deposition number KCTC11870BP, *Lactobacillus rhamnosus* with deposition number KCTC 11868BP, and *Lactobacillus paracasei* with deposition number KCTC11866BP.

There is still a need within the art to find effective preventive and therapeutic methods against osteoporosis in humans.

SUMMARY OF THE INVENTION

The present invention relates in one aspect to at least one probiotic strain chosen from Lactobacillus paracasei, or at least one probiotic strain chosen from Lactobacillus paracasei in combination with at least one probiotic strain chosen from Lactobacillus plantarum, for use in the treatment or prevention of osteoporosis or for use in increasing the absorption of $Ca^{2+}$ ions, in a mammal, preferably in a human.

BRIEF DESCRIPTION OF THE FIGURES

FIG. 3 discloses the experiment design and body weight of experiment 3. Outline of experiment design (A). Eight-week-old mice were treated with either vehicle (veh), a single Lactobacillus (L) strain (L. para) or a mixture of three strains (L. mix) during 6 weeks, starting two weeks before ovx or sham surgery. The L. strains were given in the drinking water at a concentration of $10^9$ colony-forming units (cfu)/ml while control mice received tap water with vehicle. Mice were 14-week-old at the end of the study, when tissues were collected for later analysis. Ovx resulted in an expected increased body weight compared to sham mice that was not different after probiotic treatment (B). Results are given as mean±SEM (n=9-10), **p≤0.01. Student's t test ovx vs. sham.

FIG. 4 discloses that probiotics protect mice from ovx induced cortical bone-loss. Eight-week-old mice were treated with either vehicle (veh), a single Lactobacillus (L) strain (L. para) or a mixture of three strains (L. mix) during 6 weeks, starting two weeks before ovx or sham surgery to study the preventive effect of probiotic treatment on ovx induced bone-loss. At the end of the experiment, dissected femurs were analysed with high-resolution µCT and peripheral quantitative computed tomography (pQCT). Representative µCT images of one cortical section from the veh and L. mix treated sham and ovx groups (A). Cortical bone mineral content (BMC) (B) and cortical area (C) were measured by pQCT in the mid-diaphyseal region of femur. Values are given as mean±SEM, (n=9-10). **p≤0.01, *p≤0.05. Student's t test ovx vs. sham. #p≤0.05, ANOVA followed by Dunnett's post hoc test within the groups, ovx L. Para and L. mix vs. ovx veh.

FIG. 5 discloses that probiotics reduces expression of inflammatory cytokines and the RANKL/OPG ratio in cortical bone. QRT-PCR analysis of the expression of genes known to promote bone resorption; (A) Tumor Necrosis Factor alpha (TNFα), (B) Interleukin-1β (IL-1β), (C) Interleukin-6 (IL-6), (D) Ratio of Receptor activator of nuclear factor kappa-B ligand (RANKL) and Osteoprotegerin (OPG), and individual graphs for (E) OPG, (F) RANKL and genes known to promote bone formation; (G) Osterix, (H) Collagen, type I, α1 (Col1α1) and (I) osteocalcin in cortical bone from 14-week-old ovariectomized (ovx) mice treated with either vehicle (veh) or a mixture of three probiotic Lactobacillus strains (L. mix) during 6 weeks, starting two weeks before ovx or sham surgery to study the preventive effect of probiotic treatment on ovx-induced bone-loss. Values are given as mean±SEM, n=9-10. *P≤=0.05 versus veh treatment, Student's t-test.

FIG. 6 discloses that the fractional excretion of Ca was increased by ovx in the veh treated but not in the L. para or the L. mix treated mice. Ca and creatinine were measured in serum and urine from 14-week-old mice that had been treated with vehicle (veh), a single Lactobacillus (L) strain (L. para) or a mixture of three strains (L. mix) during 6 weeks, starting two weeks before ovx or sham surgery. Urinary fractional Ca excretion was calculated with the formula FECa=(urine Ca×serum creatinine)/(serum Ca×urine creatinine). Values are given as mean±SEM, n=5-10 in each group. *p≤0.05. Student's t test ovx vs. sham. #p≤0.05, ANOVA followed by Dunnett's post hoc test within the groups, ovx L. Para and L. mix vs. ovx veh.

DESCRIPTION OF THE INVENTION

The present invention relates, in an embodiment, to at least one probiotic strain chosen from Lactobacillus paracasei, or at least one probiotic strain chosen from Lactobacillus paracasei in combination with at least one probiotic strain chosen from Lactobacillus plantarum, for use in the treatment or prevention of osteoporosis or for use in increasing the absorption of $Ca^{2+}$ ions, in a mammal, preferably in a human.

The present invention relates, in an embodiment of the invention, to at least one probiotic strain for use in the treatment or prevention of osteoporosis by preventing cortical bone loss, by preventing bone mineral content loss, and by preventing bone-resorption.

Figure 4:
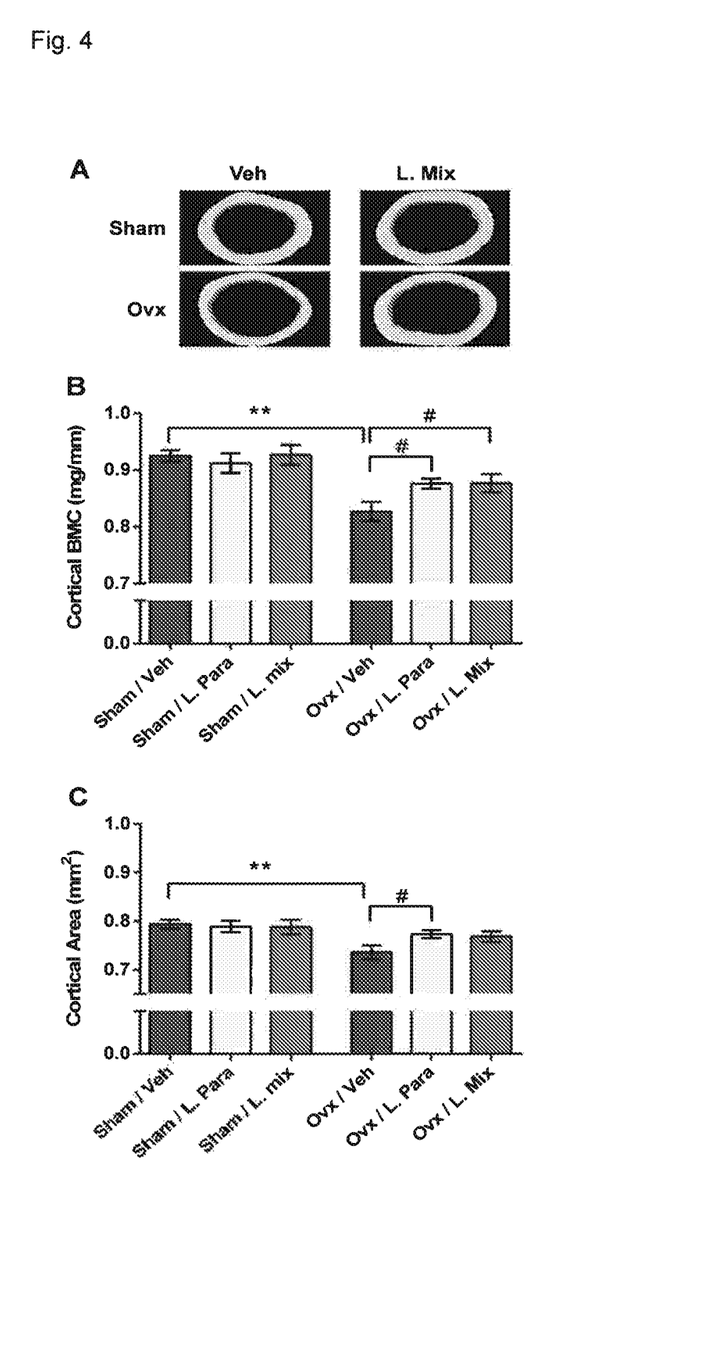

Cortical bone constitutes approximately 80% of the bone in the body and several studies have shown that cortical bone is the major determinant of bone strength and thereby fracture susceptibility. It has been shown in the experiments of the present invention that a probiotic strain of the species Lactobacillus paracasei either alone or in combination with strains of the species Lactobacillus plantarum prevents cortical bone loss. It is also indicated in the experiments of the invention that probiotic treatment alters the immune status in bone resulting in attenuated bone resorption. In addition, it is also shown in the experiments of the invention that bone mineral content was not reduced in the probiotic group compared to vehicle group (FIG. 4a-c). Bone mineral content in cortical bone was higher in both probiotic groups compared to vehicle group (p<0.05, FIG. 4b).

The present invention relates to at least one probiotic strain chosen from Lactobacillus paracasei, or at least one Lactobacillus paracasei in combination with at least one probiotic strain chosen from Lactobacillus plantarum, for use in the treatment or prevention of osteoporosis, for preventing bone mineral content loss, for preventing bone-loss in a mammal, preferably in a human.

The present invention relates to at least one probiotic strain chosen from Lactobacillus paracasei, or at least one Lactobacillus paracasei in combination with at least one probiotic strain chosen from Lactobacillus plantarum, for use in preventing bone mineral content loss, for preventing bone-loss in a mammal, preferably in a human.

In an embodiment of the invention at least two or more Lactobacillus plantarum strain are used together in a combination with at least one Lactobacillus paracasei strain. In another embodiment at least two or more, for example three or more, Lactobacillus paracasei strains are used together in a combination with at least one Lactobacillus plantarum strain.

In an embodiment of the invention the probiotic strain is viable, inactivated or dead. In an embodiment of the invention said strains are present in a composition comprising additionally at least one carrier. The carrier could be any carrier conventionally used in for instance a dietary supplement. The carrier may be any cereal based carrier such as an oatmeal carrier or barley carrier that can be used in a functional food or any other kind of food. The carrier may be water or any other aqueous solvent in which the probiotic strain is mixed before intake.

In an embodiment of the invention the composition is supplemented with additional $Ca^{2+}$ in the form of for instance a salt, e.g. calcium carbonate, calcium chloride, calcium salts of citric acid, calcium gluconate, calcium glycerophosphate, calcium lactate, calcium oxide, calcium sulphate. The recommended daily intake (ROI) of $Ca^{2+}$ is 800 mg. The amount of $Ca^{2+}$ in the composition may be in the range of 10-40% of the ROI, preferably in the range of 15-30% of the ROI. Thus, the amount of $Ca^{2+}$ e.g. in the form of a salt in the composition may be in the range 80-320 mg, preferably 120-240 mg. The amount of $Ca^{2+}$ added to the composition could be adjusted to any amount within the above range so that the composition is still stable and provides its beneficial effects.

The composition may be a dry, non-fermented composition or a fermented composition. In the case of a dry, non-fermented composition, the fermentation takes place after intake of the composition by an individual, i.e. in the gastrointestinal tract. In addition, the strains may be present in the composition as freeze-dried strains.

The probiotic strain of *Lactobacillus paracasei* may be chosen from *Lactobacillus paracasei* 8700:2, DSM 13434, and *Lactobacillus paracasei* 02:A, DSM 13432 and the probiotic strain of *Lactobacillus plantarum* may be chosen from *Lactobacillus plantarum* 299, DSM 6595, *Lactobacillus plantarum* 299v, DSM 9843, *Lactobacillus plantarum* HEAL 9, DSM 15312, *Lactobacillus plantarum* HEAL 19, DSM 15313, and *Lactobacillus plantarum* HEAL 99, DSM 15316.

*Lactobacillus paracasei* 8700:2, Accession No.: DSM 13434, and *Lactobacillus paracasei* 02:A, Accession No.: DSM 13432, were both deposited on 10 Apr. 2000 at the Deutsche Sammlung van Mikroorganimsen und Zellkulturen GmbH, Mascheroder Weg 1 b, D-38124 Braunschweig, Germany.

*Lactobacillus plantarum* HEAL 9, Accession No.: DSM 15312, *Lactobacillus plantarum* HEAL 19, Accession No.: DSM 15313, and *Lactobacillus plantarum* HEAL 99, Accession No.: DSM 15316 were deposited at the Deutsche Sammlung van Mikroorganimsen und Zellkulturen GmbH, Mascheroder Weg 1 b, D-38124 Braunschweig, Germany, on 28 Nov. 2002.

*Lactobacillus plantarum* 299v, Accession No.: DSM 9843, was deposited on 21 Mar. 1995 and *Lactobacillus plantarum* 299, Accession No.: DSM 6595, was deposited on 5 Jul. 1991 at the Deutsche Sammlung van Mikroorganimsen und Zellkulturen GmbH, Mascheroder Weg 1 b, D-38124 Braunschweig, Germany.

In an embodiment of the invention, the composition including the at least one strain may be chosen from the group consisting of a food product, a dietary supplement, a medical food, a functional food and a nutritional product.

In the case where said composition is a food product, it may be chosen from the group comprising beverages, yoghurts, juices, ice creams, breads, biscuits, cereals, health bars, and spreads.

When any of the above mentioned strains are used in a composition such as a dietary supplement the carrier(s) to be added are known to a skilled person. Any other ingredients that are normally used in dietary supplements are known to a skilled person and may also be added conventionally together with the strains.

In an embodiment of the invention, the above mentioned probiotic strain(s) are present in a composition in an amount from about $1 \times 10^6$ to about $1 \times 10^{14}$ CFU, preferably $1 \times 10^8$ to $1 \times 10^{12}$ and more preferably $1 \times 10^9$ to $1 \times 10^{11}$. The strains may be also be used alone in the above amount in water or any other aqueous vehicle in which the strains are added or mixed before intake.

The invention is suitable to be used by mammals, preferably any humans, such as elderly people, postmenopausal women and premenopausal women, in which bone loss, bone mineral content loss and increased bone-loss or bone resorption are or may become a problem.

Healthy people may naturally also benefit from the invention in order to stay healthy and prevent getting sick by osteoporosis.

EXPERIMENTAL

Experiment 1

Materials and Methods
"Transport Solutions"; Total Volume 6 ml
The transport Solutions contained Hank's Balanced Salt solution (HBSS) with Ca and Mg, Hepes (2%), Glutamine (4 mM), D-Glc (3, 5 g/l) and $CaCl_2 \cdot 2 H_2O$ (1.47 g/l). Analysis of the solution gave a $[Ca^{2+}]$ on 10.65 mM.
"Basal Solution"
Similar to the transport solution, but without the addition of external calcium. Analysis of this solution gave a $[Ca^{2+}]$ 1.22 mM.

Experiment 1

1. Control of the transport solution only
2. Lyophilised *Lactobacillus plantarum* 299 v. 0,788 mg corresponding to $4.02 \times 10^8$ bacteria/6 ml in transport solution
3. *Lactobacillus plantarum* 299v. $4.02 \times 10^8$ bacteria/6 ml in transport solution
4. *Lactobacillus plantarum* 299. $4.95 \times 10^8$ bacteria/6 ml in transport solution
5. *Lactobacillus plantarum* HEAL 19, $4.95 \times 10^8$ bacteria/6 ml in transport solution
6. AMJ 1277. $4.95 \times 10^8$ bacteria/6 ml in transport solution. AMJ 1277 is a mutated form of *Lactobacillus plantarum* 299v.

Experiment 2

1. CNCM 1-2332, *Lactobacillus acidophilus* (La10); $+4.95 \times 10^8$ bacteria/6 ml in transport solution
2. *Lactobacillus plantarum* 299 v. $4,02 \times 10^8$ bacteria/6 ml in transport solution
3. Control—transport solution only All strains except strain La10 were cultured aerobically in 30 ml of MRS. (30° C., 210 rpm). La10 was cultured in 37° C. and covered with sterile filtrated nitrogen before sealing. Number of inoculated cells was $3 \times 10^8$/flask. The bacteria were precultivated over night and were in exponential phase at inoculation. The cells were harvested at $OD_{600}$=0.1-0.5 and for each strain a volume corresponding to $4.02 \times 10^8$ cells was collected. These samples were centrifuged at 5000 rpm, 3 min, the supernatant was poured and the cells resuspended in NaCl (0.9%). The cells were centrifuged again and the supernatant was decanted. The now washed pellet was then suspended in the transport solution.

Caco-2 cells were washed with PBS (2 times) before the test. $^{45}$Ca Cl$_2$ (74 kBq/ml) were added to the transport solutions. The mixture was then added, in a volume of 0.5 ml, apically to Caco-2 cells growing on inserts. Each well has then obtained 6.7×10$^7$ bacteria/ml. Only the basal solution (1.5 ml) containing only the endogenous [Ca$^{2+}$] in HBSS (1.22 mM) was added the basal Chamber. Suspensions and controls were allowed to function on the Caco-2 cells for 2 h. They were then aspirated and the cells were washed with ice-cold washing-buffer 3 times in accordance with the method described in WO99/02170. The Caco-2 cells were thereafter lysated in 0.5 ml of NaOH (0.5 M). The solutions in the basal chambers were collected for measurement of transport with the help of scintilator (Tri-carb 2800TR, Perkin Elmer). The lysates were analyzed for $^{45}$Ca, but also for protein content. All measured values for Ca$^{2+}$ transport/uptake were normalized against the protein content in the respective cells. All wells were checked before and after incubation with the test solutions regarding transepitelial resistance (TEER). No differences in TEER, before and after the trials, could be seen. TEER is measured to ensure that the epithelium is not leeking. A difference in resistance after a trial may lead to the suspicion that the intercellular bonds may have been damaged by the solutions used.

Results

To enable comparison of the results from experiments 1 and 2, transport and uptake data from the studied strains have been normalised against the control solution without bacteria. All results are therefore presented as a percentage of the control (similarly to as done in WO99/02170). It should also be noted that the experiments 1 and 2 were done on days 16 and 21 of cellular culture, respectively. In general, it is observed that the standard deviations of the obtained results are relatively large. This could be due to some form of aggregation of bacteria and Ca$^{2+}$, leading to a variation in the availability of Ca$^{2+}$. This is not observed for the freeze-dried bacteria where the standard deviations were relatively small compared with the remaining samples.

Transport of Ca$^{2+}$

Figure 1:
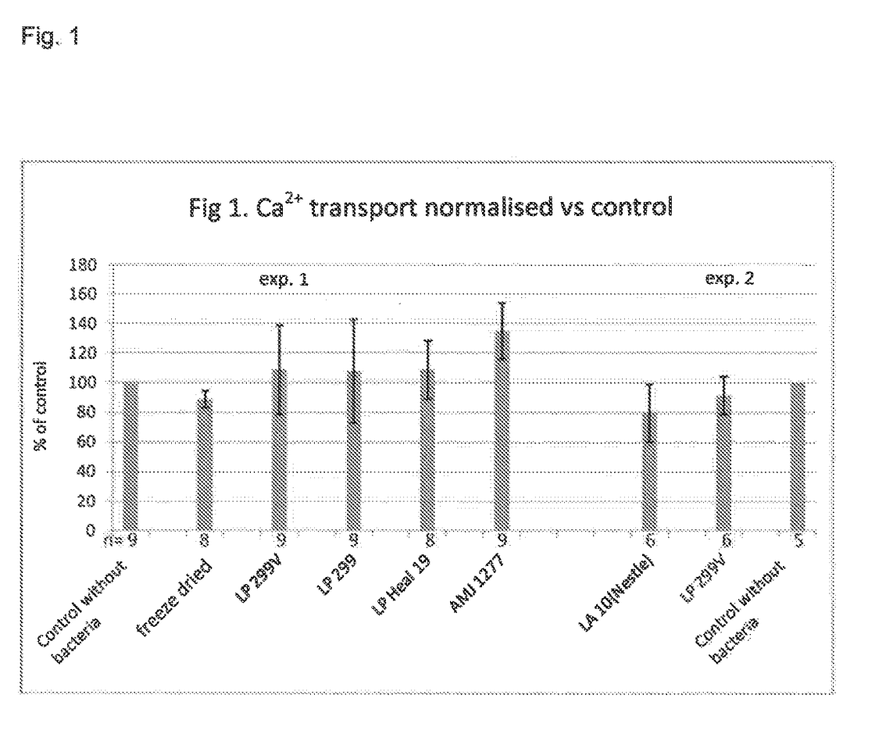
FIG. 1 discloses $Ca^{2+}$ transport tested with the different bacterial strains as disclosed in experiment 1 and 2.

The results of experiment 1 showed a significant improvement of the Ca$^{2+}$ transport when the strain AMJ1277 was present (134.7±18.9%, p=0.002), see FIG. 1. None of the other strains (Lp299v freeze-dried and viable, Lp299, Lp HEAL 19) gave significant differences in transport of Ca$^{2+}$, se table 1. In experiment 2 where La10 and Lp299v were tested no significant differences in the transport of Ca$^{2+}$ were detected when comparing the samples with Lp299v vs control without bacteria (p=0.2). For La10 a slight decrease of the Ca$^{2+}$ transport in the presence of the same bacteria was observed (79.5±19.3%) and this change was significant (p=0.049).

Uptake of Ca$^{2+}$

Figure 2:
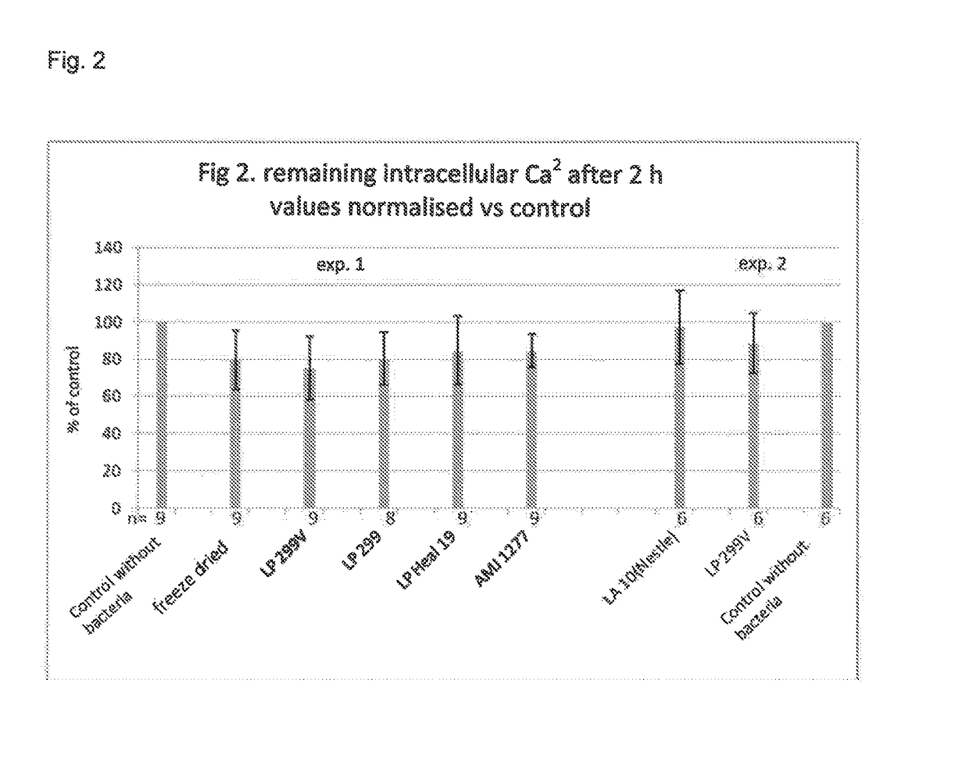
FIG. 2 discloses the remaining intracellular $Ca^{2+}$ in the cells after 2 h as described in the experiments 1 and 2.

Uptake data presented here show the amount of Ca$^{2+}$ present in the cells after 2 hrs. For an estimate of the actual uptake data, the intracellular amounts of Ca$^{2+}$ should be added to the amount of Ca$^{2+}$ detected in the lateral compartments. The sum of these data describes the total amount of Ca$^{2+}$ that has been transported through the apical membrane. The results of these experiments generally shows a reduction in intracellular [Ca$^{2+}$] in the presence of bacteria, compared to the bacteria-free control solutions, see FIG. 2. However, only the differences of the lyophilized and viable Lp299v, were significant (p=0.04 and p=0.02). Note, that the intermediate intracellular Ca$^{2+}$ levels are only a few percent in comparison to the transported amount of Ca$^{2+}$. Due to this, the demonstrated effect of the uptake of Ca$^{2+}$ do not have the same impact as the effects on transport. This can be observed for lyophilized and viable Lp 299v, which has a higher intracellular [Ca$^{2+}$] but do not demonstrate an improvement in transport.

Conclusion

In the presence of the strain AMJ1277, a mutant *Lactobacillus plantarum* 299v, an increased transport and even a total uptake of calcium is observed compared to both the control and the remaining strains. Thus, there is variation between the strains looked at.

Experiment 3

Ovariectomized Mouse-Model and Probiotic Treatment

Ovariectomy (ovx) results in bone loss associated with altered immune status. The purpose of this experiment was to determine if probiotic treatment protects mice from ovx induced bone loss. Mice were treated with either a single *Lactobacillus* (L) strain, *L. paracasei* DSM13434 (*L. para*) or a mixture of three strains, *L. paracasei* DSM13434, *L. plantarum* DSM 15312 and DSM 15313 (L. mix) given in the drinking water during 6 weeks, starting two weeks before ovx.

Six-week old C57BL/6N female mice were purchased from Charles River (Germany). The mice were housed in a standard animal facility under controlled temperature (22° C.) and photoperiod (12-h light, 12-h dark) and had free access to fresh water and soy-free food pellets R70 (Lactamin AB, Stockholm, Sweden). The ovariectomized (ovx) model for osteoporosis is included in the FDA guidelines for preclinical and clinical evaluation for agents used for the treatment of postmenopausal osteoporosis. Probiotic treatment started two weeks before ovx to study the preventive effect of probiotic treatment on ovx induced bone-loss. Mice were treated with either a single *Lactobacillus* (L) strain, *L. paracasei* DSM13434 (*L. para*) or a mixture of three strains, *L. paracasei* DSM13434, *L. plantarum* DSM 15312 and DSM 15313 referred to as L. mix during 6 weeks. The probiotic strains were selected based on their anti-inflammatory properties. The L. strains were given in the drinking water at a concentration of 10$^9$ colony-forming units (cfu)/ml while control mice received tap water with vehicle. Water bottles were changed every afternoon. The survival of the L. strains in the water bottles was checked regularly and after 24 h the concentration dropped one log unit to approximately 10$^8$ cfu/ml. Each mouse drank on average 4.5 ml water/day. After two weeks of probiotic treatment, the mice were either sham-operated or ovx under inhalation anesthesia with isoflurane (Forene; Abbot Scandinavia, Solna, Sweden). Four weeks after surgery, blood was collected from the axillary vein under anesthesia with Ketalar/Domitor vet, and the mice were subsequently killed by cervical dislocation. Tissues for RNA preparation were immediately removed and snap-frozen in liquid nitrogen for later analysis. Bones were excised and fixed in 4% paraformaldehyde. All animal experiments had been approved by the local Ethical Committees for Animal Research at the University of Gothenburg.

Peripheral Quantitative Computed Tomography (pQCT)

Computed tomographic scans were performed with the pQCT XCT RESEARCH M (version 4.5B, Norland, Fort Atkinson, Wis., USA) operating at a resolution of 70 µm, as.

Cortical bone parameters were analyzed ex vivo in the mid-diaphyseal region of the femur.

High-Resolution μCT

High-resolution μCT analyses were performed on the distal femur by using an 1172 model μCT (Bruker micro-CT, Aartselaar, Belgium). The femurs were imaged with an X-ray tube voltage of 50 kV and current of 201 μA, with a 0.5-mm aluminium filter. The scanning angular rotation was 180° and the angular increment 0.70°. The voxel size was 4.48 μm isotropically. The NRecon (version 1.6.9) was employed to perform the reconstruction following the scans. In the femur, the trabecular bone proximal to the distal growth plate was selected for analyses within a conforming volume of interest (cortical bone excluded) commencing at a distance of 538.5 μm from the growth plate, and extending a further longitudinal distance of 134.5 μm in the proximal direction. Cortical measurements were performed in the diaphyseal region of femur starting at a distance of 3.59 mm from the growth plate and extending a further longitudinal distance of 134.5 μm in the proximal direction. For BMD analysis, the equipment was calibrated with ceramic standard samples.

RNA Isolation and Real Time PCR

Total RNA was prepared from cortical bone (femur with the ends removed and bone marrow flushed out with PBS before freezing) and bone marrow using TriZol Reagent (Invitrogen, Lidingo, Sweden). The RNA was reverse transcribed into cDNA using High-Capacity cDNA Reverse Transcription Kit (#4368814, Applied Biosystems, Stockholm, Sweden). RT-PCR analyses were performed using the ABI Prism 7000 Sequence Detection System (PE Applied Biosystems). We used predesigned RT-PCR assays from Applied Biosystems (Sweden) for the analysis of IL-6 (Mm00446190_m1), IL-1β (Mm00434228_m1), TNFα (Mm00443258_m1), RANKL (Mm00441908_m1), OPG (Mm00435452_m1), Runx2 (Mm00501580_m1), Col1α1 (Mm00801666_g1), osteocalcin (Mm01741771_g1) and TGFβ1 (Mm03024053_m1) mRNA levels. The mRNA abundance of each gene was calculated using the "standard curve method" (User Bulletin 2; PE Applied Biosystems) and adjusted for the expression of 18S (4308329) ribosomal RNA.

Blood Analysis

Analyses were performed according to the manufacturer's instructions for serum and urine calcium (QuantiChrom™ Calcium Assay Kit (DICA-500), Bioassays systems, Hayward, Calif., USA), serum and urine creatinine (Mouse Creatinine Kit, Crystal Chem, Downers Grove, Ill., USA). As a marker of bone resorption, serum levels of type I collagen fragments were assessed using a RatLaps ELISA kit (Nordic Bioscience Diagnostics, Herlev, Denmark). Serum levels of osteocalcin, a marker of bone formation, were determined with a mouse osteocalcin immunoradiometric assay kit (Immutopics, San Clemente, Calif.).

Flow Cytometry

Bone marrow cells were harvested by flushing 5 ml PBS through the bone cavity of one femur using a syringe. After centrifugation at 515 g for 5 min, pelleted cells were resuspended in Tris-buffered 0.83% $NH_4Cl$ solution (pH 7.29) for 5 min to lyse erythrocytes and then washed in PBS. Bone marrow cells were resuspended in RPMI culture medium (PAA Laboratories, Pasching, Austria) before use. The total number of leucocytes in bone marrow was calculated using an automated cell counter (Sysmex, Hamburg, Germany). For flow cytometry analyses, cells were stained with allophycocyanin (APC)-conjugated antibodies to CD4 for detection of T helper cells (Beckton-Dickinson) and fluorescein isothiocyanate (FITC)-conjugated antibodies to CD8 cytotoxic T cells (Beckton-Dickinson) or Peridinin-chlorophyll proteins (PerCP)-conjugated antibodies to Gr-1/Ly-6G (BioLegend) to eliminate granulocytes and FITC-conjugated antibodies to CD11b for detection of OCL precursor cells (Beckton-Dickinson). The cells were then subjected to fluorescence activated cell sorter analysis (FACS) on a FACSCalibur (BO Pharmingen, Franklin Lakes, N.J. USA) and analyzed using FlowJo software. Results are expressed as cell frequency (%).

Statistical Analyses

All the statistical results are presented as the means±SEM. Between-group differences were calculated using unpaired t tests. Comparisons between multiple groups were calculated using a one-way analysis of variance (ANOVA) followed by Dunnett's test to correct for multiple comparisons. A two-tailed p 0.05 was considered significant.

Figure 3:
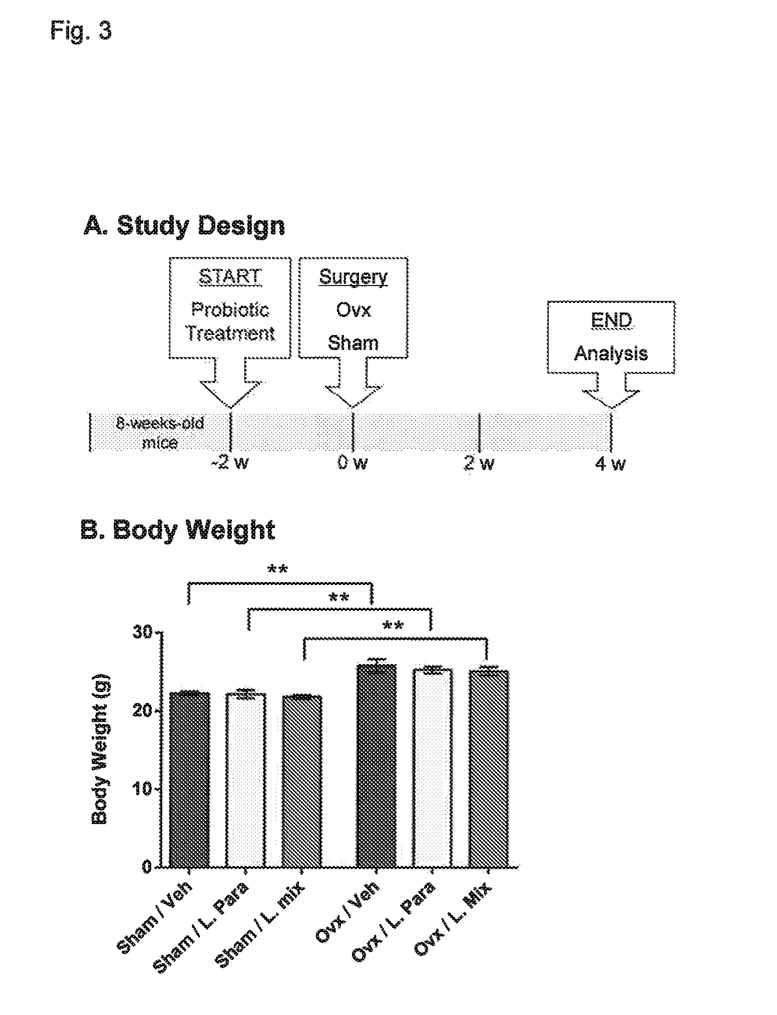

Results—Probiotic Treatment Protects Mice from Ovx-Induced Cortical Bone Loss and Increased Bone Resorption To determine the preventive effect of probiotic treatment on ovx-induced bone-loss, eight-week-old mice were treated with vehicle (veh), a single *Lactobacillus* (L) strain (*L. para*) or a mixture of three strains (L. mix) during 6 weeks, starting two weeks before ovx or sham surgery (FIG. 3A). Uterus weight can be used as an indicator of estrogen status and ovx resulted in an expected decrease in uterus weight that was similar for all treatments (Table 2). In addition, ovx increased body weight, fat mass and thymus weight in all treatment groups (FIG. 3B, Table 2).

In the vehicle treated mice, ovx decreased the cortical bone mineral content and cortical cross sectional bone area in the mid-diaphyseal region of femur (p<0.01, FIG. 4a-c). Importantly, ovx did not reduce cortical bone mineral content or cortical cross sectional bone area in the *L. para* or the L. mix treated mice (FIG. 4a-c). Cortical bone mineral content was higher in both *L. para* and L. mix treated ovx mice compared to veh treated ovx mice (p<0.05, FIG. 4b). To determine if the preventive effect of probiotics on cortical bone is caused by affected bone resorption, serum levels of C-terminal telopeptides (RatLaps) were analyzed. Ovx increased levels of RatLaps in veh-treated mice (+45±11%, p<0.05 over sham) but not in *L. para* treated (20±9%, non-significant) or L. mix treated (23±9%, non-significant) mice. Bone formation, as indicated by serum osteocalcin, was not significantly affected by probiotic treatment (data not shown). Trabecular bone parameters (BV/TV and trabecular BMD) in the distal metaphyseal region of femur were significantly reduced by ovx in all treatment groups (p<0.05 Table 1). These findings demonstrate that probiotic treatment protects mice from ovx-induced cortical bone loss and increased bone resorption.

Figure 5:
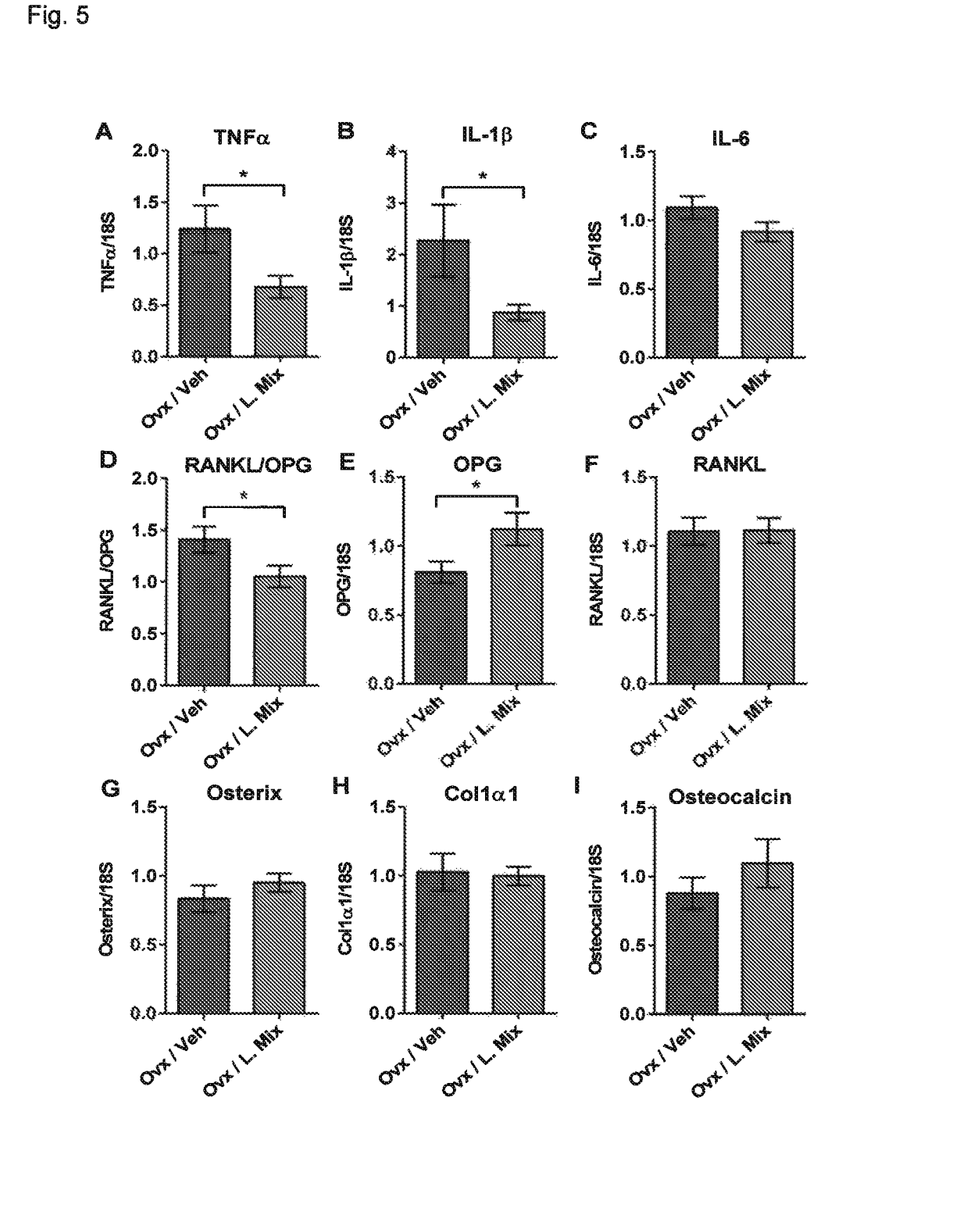

Probiotics Reduces Expression of Inflammatory Cytokines and the RANKL/OPG Ration in Cortical Bone To investigate the mechanism for the effect of probiotic treatment on ovx-induced cortical bone loss, we measured bone related mRNA transcripts in cortical bone (FIG. 5). The mRNA levels of TNFα, an inflammatory cytokine produced by myeloid cells that promotes osteoclastogenesis, and IL-1β, a downstream regulator of the effects of TNFα on bone, were significantly decreased by probiotic treatment compared to vehicle treatment in ovx mice (TNFα—46%, p<0.05; IL-1β—61%, p<0.05, FIGS. 5a and 5b). The expression of, IL-6 did not differ between treatments although there was a tendency to decreased expression in the probiotic treatment group (−20%, p=0.12, FIG. 5c).

The RANKL/osteoprotegerin (OPG) ratio is a major determinant of osteoclastogeneisis and, thereby, bone resorption. Importantly, probiotic treatment decreased the RANKL/OPG ratio (−45%, p<0.05 compared with veh, FIG. 5d) and this was caused by an increased OPG expression (OPG; +28%, p<0.05 and RANKL; +1%, non-significant, FIG. 5e, f). In contrast, the mRNA levels of three osteoblast-associated genes, Osterix, Col1α1 and osteocalcin, were not affected by probiotic treatment (FIGS. 5g-h).

Immune Status in Bone Marrow

Some of the anti-inflammatory effects exerted by probiotic bacteria are thought to be mediated via the induction of regulatory T ($T_{reg}$) cells. FACS analysis of bone marrow showed that the frequency of $T_{reg}$ (CD4$^+$ CD25$^+$ Foxp3$^+$) cells was decreased by ovx in veh treated but not in probiotic-treated mice (Table 2). $T_{reg}$ cells are dependent on TGFβ for their induction and maintenance and the expression of TGF61 was increased in bone marrow from ovx probiotic-treated compared with ovx vehicle treated mice (+77±19%, p<0.01).

It was also examined if probiotic treatment modulated the frequency of osteoclast precursor cells (preOCLs) in bone marrow. The frequency of preOCLs (CD11b$^+$ Gr1$^-$) in bone marrow was not affected by ovx in any of the treatment groups (Table 2).

Mineral Metabolism

Figure 6:
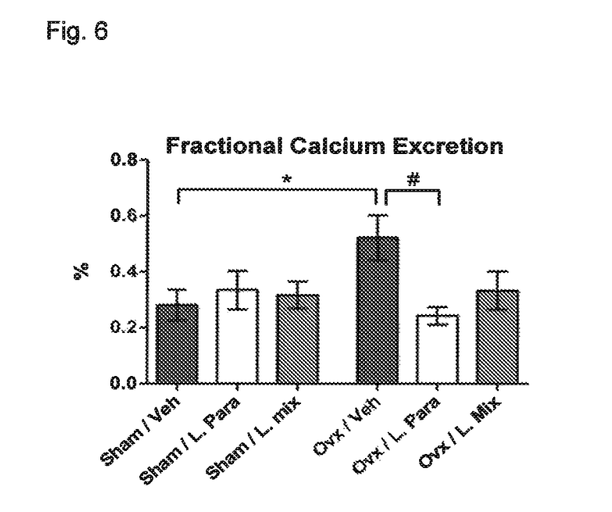

The urinary fractional excretion of Calcium (FECa=(urine Ca×plasma creatinine)/(plasma Ca×urine creatinine)) was increased by ovx in veh treated mice (+86%, p<0.05, FIG. 6). The ovx induced increase in FECa was completely prevented by probiotic treatment suggesting enhanced accretion of Ca (FIG. 6). There was a tendency of increased serum levels of Ca after ovx in veh but not probiotic treated mice (+13%, p=0.05, Table 3). The urine Ca/creatinine ratio was not affected by ovx in any of the treatment groups (Table 3).

TABLE 1

| | Transport | | | | | intracellular Ca (2 h) | | | | |
|---|---|---|---|---|---|---|---|---|---|---|
| | (μmol/mg prot) | | % of control | | | (μmol/mg prot) | | % of control | | |
| Strain | Average | sdev (±) | Average | sdev (±) | *p = | Average | sdev (±) | average | sdev (±) | *p = |
| control without bact. | 0.14822 | 0.03254 | 100 | x | 1 | 0.010295 | 0.002456 | 100 | x | 1 |
| Freeze-dried Lp 299v | 0.131773 | 0.0217772 | 88.903807 | 5.771665 | 0.246025 | 0.008195 | 0.001638 | 79.60091 | 15.90269 | 0.048654 |
| Lp 299v (1) | 0.161124 | 0.0439384 | 108.70637 | 29.68811 | 0.489095 | 0.00777 | 0.001767 | 75.47339 | 17.15187 | 0.023494 |
| Lp 299 | 0.159745 | 0.0517202 | 107.77569 | 34.9461 | 0.579356 | 0.008296 | 0.001452 | 80.58207 | 14.09352 | 0.063082 |
| Lp heal 19 | 0.161361 | 0.0291023 | 108.866 | 19.66369 | 0.497942 | 0.008736 | 0.001901 | 84.85697 | 18.45752 | 0.151598 |
| AMJ1277 | 0.199657 | 0.0279951 | 134.70331 | 18.91582 | 0.002 | 0.008744 | 0.000942 | 84.9374 | 9.141623 | 0.096014 |
| La 10 | 0.182937 | 0.0443204 | 79.537982 | 19.26973 | 0.049 | 0.015901 | 0.003197 | 97.43651 | 19.61249 | 0.826775 |
| Lp 299v (2) | 0.210131 | 0.0289741 | 91.361137 | 12.59742 | 0.2 | 0.014491 | 0.002629 | 88.79696 | 16.12947 | 0.309532 |
| control without bact | 0.229676 | 0.0111063 | 100 | x | 1 | 0.016319 | 0.003254 | 100 | x | 1 |

*if p < 0.05 the change is seen as significant

TABLE 2

Table 1. Estrogen Responsive Organ Weights, Trabecular Bone and Immune Cells in Bone Marrow Eight-week-old mice. Trabecular bone parameters were analysed by high resolution μCT in the distal metaphyseal region of femur; Trabecular bone volume as a percentage of tissue volume (BV/TV); Trabecular bone mineral density (BMD). Femur bone marrow cells were stained with antibodies recognizing CD4, Foxp3, CD25, CD11b and Gr1. Values represent the percentage of Treg (CD4+ Foxp3+ CD25+) or preOCLs (CD11b+ Gr1−) in the total bone marrow population.

| | Sham | | | Ovx | | |
|---|---|---|---|---|---|---|
| | Veh | L. Para | L. Mix | Veh | L. Para | L. Mix |
| Estrogen Responsive Organ Weights | | | | | | |
| Uterus weight (mg) | 45.9 ± 4.8 | 65.9 ± 12.5 | 65.2 ± 10.4 | 8.95 ± 0.7** | 11.0 ± 3.2** | 6.9 ± 0.3** |
| Gonadal Fat (mg) | 371 ± 41 | 296 ± 40 | 326 ± 40 | 597 ± 68* | 630 ± 28** | 577 ± 58** |
| Thymus weight (mg) | 55.5 ± 3.2 | 53.6 ± 5.1 | 47.7 ± 2.6 | 93.9 ± 4.2** | 90.0 ± 5.1** | 73.7 ± 5.2**# |
| Trabecular Bone | | | | | | |
| BV/TV (%) | 16.2 ± 0.7 | 16.8 ± 0.8 | 17.4 ± 0.8 | 13.2 ± 0.7** | 14.4 ± 0.6* | 13.8 ± 0.5** |
| BMD (mg/cm$^3$) | 322 ± 9 | 331 ± 12 | 344 ± 8 | 285 ± 9* | 302 ± 7* | 298 ± 7** |
| Immune Cells in Bone marrow | | | | | | |
| $T_{reg}$ (CD4+ Foxp3+ CD25+) (%) | 0.117 ± 0.023 | 0.109 ± 0.017 | 0.090 ± 0.017 | 0.054 ± 0.004* | 0.069 ± 0.008 | 0.070 ± 0.014 |
| preOCLs (CD11b$^+$ Gr1$^-$) (%) | 7.77 ± 1.01 | 6.75 ± 1.20 | 8.94 ± 1.17 | 6.70 ± 0.94 | 7.17 ± 1.32 | 8.57 ± 1.50 |

Results are given as mean ± SEM,
n = 6-10 in each group.
**p < 0.01,
*p < 0.05,
Student's t test ovx vs. sham,
p < 0.05,
ANOVA-Dunnets within groups.

TABLE 3

Table 2. Mineral Metabolism Calcium and creatinine were measured in serum and urine from 14-week old mice.

| | | Sham | | | Ovx | | |
|---|---|---|---|---|---|---|---|
| | | Veh | L. Para | L. Mix | Veh | L. Para | L. Mix |
| Serum | Ca (mg/dl) | 9.1 ± 0.4 | 9.2 ± 0.4 | 8.5 ± 0.3 | 10.3 ± 0.4(*) | 9.3 ± 0.4 | 8.7 ± 0.3# |
| Urine | Ca/Creatinine Ratio | 6.7 ± 0.7 | 6.3 ± 0.4 | 5.4 ± 0.6 | 8.5 ± 1.3 | 5.9 ± 0.5 | 5.6 ± 0.7 |

Results are given as mean ± SEM,
n = 5-10 in each group.
**$p < 0.01$,
*$p < 0.05$,
(*)$p = 0.05$.
Student's t test ovx vs. sham,
$p < 0.05$,
ANOVA-Dunnets within groups.

In conclusion, the data of the present invention show that probiotics in the drinking water reduces ovx induced cortical bone-loss suggesting a therapeutic potential for probiotics in the treatment of postmenopausal osteoporosis. In addition, the results support a role of the gut microbiota for the regulation of bone mass.

Both the L. para and the L. mix treatment protected mice from ovx-induced cortical bone loss and increased bone resorption. Cortical bone mineral content was higher in both L. para and L. mix treated ovx mice compared to vehicle (veh) treated ovx mice. The urinary fractional excretion of calcium and the resorption marker Ratlaps were increased by ovx in the veh treated but not in the L. para or the L. mix treated mice. Thus, probiotics inhibit ovx induced excretion of calcium in urine. Probiotic treatment reduced the expression of the two inflammatory cytokines, TNFα and IL-1β, and increased the expression of OPG in cortical bone of ovx mice. In addition, ovx decreased the frequency of regulatory T-cells (CD4+ CD25+ Foxp3+) in bone marrow of veh treated but not probiotic treated mice. Thus, probiotics inhibit the ovx induced decrease in frequency of regulatory T-cells in bone marrow. In addition, probiotics increased the expression of TGFb1 in bone marrow and probiotics inhibit the ovx induced increase of the resorption marker Rat Lap. In conclusion, treatment with L. para or the L. mix prevents ovx induced cortical bone loss. The findings of the invention indicate that these probiotic treatments alter the immune status in bone as demonstrated by reduced expression of inflammatory cytokines and increased expression of OPG, resulting in attenuated bone resorption in ovx mice.

Experiment 4

In this experiment it will be tested if the same probiotics as mentioned above will affect the same parameters as above (i.e. cortical bone mass, bone mineral content, bone resorption) in female mice that already have been ovariectomized and thus already have lost bone-mass. Ovariectomized female mice is a well established model of postmenopausal bone loss in women. The time line of the experiments will be as indicated below. Ovariectomize mice=>4 weeks=>Probiotic treatment for 6 weeks=>End Probiotics will be given in drinking water and will begin first after 4 weeks after ovariectomization. Dose will be $10^9$ cfu/ml/day and ovariectomization will take place at 9-10 weeks of age. Analyses after ended experiment will be (CT) of the bone to measure the density and thickness, as well as serum analysis and bone markers.

The invention claimed is:

1. A method for treating or inhibiting osteoporosis, treating or inhibiting bone loss, or increasing the absorption of $Ca^{2+}$ ions, comprising orally administering to a mammal a composition comprising a therapeutically effective amount of at least one probiotic strain selected from the group consisting of *Lactobacillus paracasei* 8700:2, DSM 13434, and *Lactobacillus paracasei* 02:A, DSM 13432, wherein the composition is supplemented with additional $Ca^{2+}$ in the form of a salt, wherein the inhibition of osteoporosis or bone loss is by reducing osteoporosis or bone loss compared to osteoporosis or bone loss without administration of said composition, and wherein increasing the absorption of $Ca^{2+}$ ions is compared to absorption of $Ca^{2+}$ ions without administration of said composition.

2. The method of claim 1, wherein said mammal is a human.

3. The method of claim 1, wherein the treatment or inhibition of osteoporosis comprises inhibiting one or more of cortical bone loss, bone mineral content loss, and bone-resorption.

4. The method of claim 1, wherein said at least one probiotic strain of *Lactobacillus paracasei* is provided in combination with at least one probiotic strain of *Lactobacillus plantarum*.

5. The method of claim 4, wherein said at least one probiotic strain of *Lactobacillus plantarum* is one or more selected from the group consisting of *Lactobacillus plantarum* 299, DSM 6595, *Lactobacillus plantarum* 299v, DSM 9843, *Lactobacillus plantarum* HEAL 9, DSM 15312, *Lactobacillus plantarum* HEAL 19, DSM 15313, and *Lactobacillus plantarum* HEAL 99, DSM 15316.

6. The method of claim 1, wherein said at least one probiotic strain(s) is present in a composition comprising at least one carrier.

7. The method of claim 6, wherein said carrier is selected from the group consisting of a food product, a dietary supplement, a medical food, a functional food, and a nutritional product.

8. The method of claim 1, wherein at least one of said probiotic strain(s) is present in an amount from about $1 \times 10^6$ to about $1 \times 10^{14}$ CFU.

9. The method of claim 8, wherein at least one of said probiotic strain(s) is present in an amount from about $1\times10^8$ to $1\times10^{12}$ CFU.

10. The method of claim 8, wherein at least one of said probiotic strain(s) is present in an amount from about $1\times10^9$ to $1\times10^{11}$ CFU.

11. The method of claim 1, wherein the method is for treating or inhibiting osteoporosis, treating or inhibiting bone loss, or increasing the absorption of $Ca^{2+}$ ions, in a woman.

12. The method of claim 5, wherein said at least one probiotic strain comprises *Lactobacillus paracasei* 8700:2, DSM 13434, in combination with *Lactobacillus plantarum* HEAL 9, DSM 15312, and *Lactobacillus plantarum* HEAL 19, DSM 15313.

13. The method of claim 11, wherein the method is for treating or inhibiting osteoporosis, treating or inhibiting bone loss, or increasing the absorption of $Ca^{2+}$ ions, in a premenopausal or postmenopausal woman.

14. The method of claim 1, wherein the salt is selected from the group consisting of calcium carbonate, calcium chloride, calcium salts of citric acid, calcium gluconate, calcium glycerophosphate, calcium lactate, calcium oxide, and calcium sulphate.

15. A method for treating or inhibiting osteoporosis, treating or inhibiting bone loss, or increasing the absorption of $Ca^{2+}$ ions, in a woman, comprising orally administering to a woman a therapeutically effective amount of at least one probiotic strain selected from the group consisting of *Lactobacillus paracasei* 8700:2, DSM 13434, and *Lactobacillus paracasei* 02:A, DSM 13432, wherein the inhibition of osteoporosis or bone loss is by reducing osteoporosis or bone loss compared to osteoporosis or bone loss without administration of said at least one probiotic strain, and wherein increasing the absorption of $Ca^{2+}$ ions is compared to absorption of $Ca^{2+}$ ions without administration of said composition.

16. The method of claim 15, wherein the woman is a premenopausal or postmenopausal woman.

17. The method of claim 15, wherein the treatment or inhibition of osteoporosis comprises inhibiting one or more of cortical bone loss, bone mineral content loss, and bone-resorption.

18. The method of claim 15, wherein said at least one probiotic strain of *Lactobacillus paracasei* is provided in combination with at least one probiotic strain of *Lactobacillus plantarum*.

19. The method of claim 18, wherein said at least one probiotic strain of *Lactobacillus plantarum* is one or more selected from the group consisting of *Lactobacillus plantarum* 299, DSM 6595, *Lactobacillus plantarum* 299v, DSM 9843, *Lactobacillus plantarum* HEAL 9, DSM 15312, *Lactobacillus plantarum* HEAL 19, DSM 15313, and *Lactobacillus plantarum* HEAL 99, DSM 15316.

20. The method of claim 19, wherein said at least one probiotic strain comprises *Lactobacillus paracasei* 8700:2, DSM 13434, in combination with *Lactobacillus plantarum* HEAL 9, DSM 15312 and *Lactobacillus plantarum* HEAL 19, DSM 15313.

21. The method of claim 15, wherein said at least one probiotic strain(s) is present in a composition comprising at least one carrier.

22. The method of claim 21, wherein said carrier is selected from the group consisting of a food product, a dietary supplement, a medical food, a functional food, and a nutritional product.

23. The method of claim 15, wherein at least one of said probiotic strain(s) is present in an amount from about $1\times10^6$ to about $1\times10^{14}$ CFU.

24. The method of claim 23, wherein at least one of said probiotic strain(s) is present in an amount from about $1\times10^8$ to about $1\times10^{12}$ CFU.

25. The method of claim 24, wherein at least one of said probiotic strain(s) is present in an amount from about $1\times10^9$ to about $1\times10^{11}$ CFU.

26. The method of claim 15, wherein said composition is supplemented with additional $Ca^{2+}$ in the form of a salt.

27. The method of claim 26, wherein the salt is selected from the group consisting of calcium carbonate, calcium chloride, calcium salts of citric acid, calcium gluconate, calcium glycerophosphate, calcium lactate, calcium oxide, and calcium sulphate.

28. The method of claim 2, wherein the human is healthy.

29. The method of claim 11, wherein the woman is healthy.

30. The method of claim 15, wherein the woman is healthy.

* * * * *